US006957151B2

(12) United States Patent
Cheng et al.

(10) Patent No.: US 6,957,151 B2
(45) Date of Patent: Oct. 18, 2005

(54) SYSTEM AND METHOD FOR AQUEOUS SOLUBILITY PREDICTION

(75) Inventors: Ailan Cheng, State College, PA (US); Kenneth M. Merz, Jr., Port Matilda, PA (US)

(73) Assignee: Accelrys Software Inc., San Diego, CA (US)

(*) Notice: Subject to any disclaimer, the term of this patent is extended or adjusted under 35 U.S.C. 154(b) by 408 days.

(21) Appl. No.: 10/195,844

(22) Filed: Jul. 12, 2002

(65) Prior Publication Data

US 2003/0028330 A1 Feb. 6, 2003

Related U.S. Application Data

(60) Provisional application No. 60/305,293, filed on Jul. 13, 2001.

(51) Int. Cl.$^7$ .................................................. G06F 9/06
(52) U.S. Cl. .......................... 702/30; 702/31; 702/183; 702/190
(58) Field of Search ............................. 702/22, 30, 31, 702/121, 155, 179, 183, 188; 356/301; 435/7.1, 174

(56) References Cited

U.S. PATENT DOCUMENTS

| | | | | |
|---|---|---|---|---|
| 6,606,567 B2 | * | 8/2003 | Grate et al. | 702/22 |
| 2002/0040276 A1 | * | 4/2002 | Ewing et al. | 702/19 |
| 2002/0061540 A1 | * | 5/2002 | Grass et al. | 435/7.1 |

OTHER PUBLICATIONS

Lipinski et al., "Experimental and Computational Approaches to Estimate Solubility and Permeability in Drug Discovery and Development Setting", (1997) Advanced Drug Delivery Reviews Amsterdam, NL, vol. 23 No. 1/3 pp. 3–25.

G. Seu, "Structure–Affinity Relationships in Aminoazo Disperse Dyes. A Multivariate Approach", (1998) Dyes and Pigments, Elsevier Applied Science Publishers, vol. 37 No. 2 pp. 103–112.

Jorgensen et al., "Prediction of Drug Solubility from Monte Carlo Simulations" (2000) Bioorganic & Medical Chemistry Letters, Oxford, GB, vol. 10 No. 11 pp. 1155–1158.

Nirmalakhandan et al., "Prediction of Aqueous Solubility of Organic Chemicals Based on Molecular Structure", (1988) Environmental Science & Technology vol 22, No. 3 pp. 328–338.

Abraham et al., "The Correlations and Prediction of the Solubility of Compounds in Water Using an Amended Solvation Energy Relationship" (1999) Jouranl of Pharmaceutical Sciences, vol. 88, No. 9 pp. 868–880.

Bodor et al., "A New Method for teh Estimation of the Aqueous Solubility of Organic Compounds" (1992) Journal of Pharmaceutical Sciences Bol. 81, No. 9 pp. 954–960.

Hall, "Electropological State Indices for Atom Types: A Novel Combination of Electronic, Topological, and Valence State Information" (1995) J. Chem Inf. Comput. Sci 35, 1039–1045.

(Continued)

Primary Examiner—Marc S. Hoff
Assistant Examiner—Felix Suarez
(74) Attorney, Agent, or Firm—Knobbe Martens Olson & Bear LLP

(57) ABSTRACT

The present teachings describe a solubility prediction approach that is based, in part, upon quantitative-structure property relationships (QSPR). In various embodiments, the solubility prediction methodology comprises identifying a reduced descriptor set from which a solubility equation is derived. The descriptors used in the solubility equation are based upon simplified structural and molecular features which facilitate researcher understanding and solubility model refinement. Moreover, the present teachings provide solubility prediction relationships that may be used to rapidly screen large libraries or collections of compounds.

72 Claims, 7 Drawing Sheets

OTHER PUBLICATIONS

Huuskonen et al., "Aqueous Solubility Prediction of Drugs Based on Molecular Topology and Neural Network Modeling" (1998) J. Chem Inf. Comput. Sci. 38 450–456.

Mitchell et al., "Prediction of Aqueous Solubility of Organic Compounds from Molecular Structure" (1998) J. Chem. Inf. Comput. Sci. 38, 489–496.

Nelson et al., "Prediction of Aqueous Solubility of Organic Compounds" (1994) J. Chem. Inf. Comput. Sci., 34, 601–609.

Sutter et al., "Prediction of Aqueous Solubility for a Diverse Set of Heteroatom–Containing Organic Compounds Using a Quantitative Structure—Property Relationship" (1996) J. Chem. Inf. Comput. Sci. 36, 100–107.

Yalkowsky et al., "Aqueous Solubility Method of Estimation for Organic Compounds", (1992) Marcel Dekker, Inc., pp. 41–148.

* cited by examiner

REGRESSION ANALYSIS TO IDENTIFY SOLUBILITY EQUATION

- 210: SELECT STATISTICAL METHOD
- 220: PERFORM STATISTICAL ANALYSIS USING SELECTED METHOD
- 230: EVALUATE STATISTICAL SIGNIFICANCE
- 240: GENERATE SOLUBILITY EQUATION

FIG. 2

SYSTEM AND METHOD FOR AQUEOUS SOLUBILITY PREDICTION

CLAIM OF PRIORITY

This U.S. patent application claims priority to U.S. Provisional Patent Application No. 60/305,293 entitled "System and Method for Aqueous Solubility Prediction" filed Jul. 13, 2001 which is hereby incorporated by reference.

BACKGROUND OF THE INVENTION

1. Field of the Invention

The present teachings generally relate to the field of solubility determination and, more particularly, to a system and method for predicting aqueous solubility.

2. Description of the Related Art

In the field of drug development, screening methods are often utilized to profile large collections of synthesized and virtual libraries for candidate compounds of pharmaceutical interest. During the screening process, the solubility of a selected compound may be assessed and represents an important consideration in terms of compound synthesis/processing, pharmacokinetic analysis, and evaluation of potential toxicity. Accurate solubility prediction is also useful in characterizing drug candidates and evaluating how functional group derivatives of the drug may be absorbed and distributed within a biological system.

Conventional methods for predicting solubility are typically not well suited for evaluating large numbers of compounds and may limit the speed and efficiency of drug discovery. A summary of selected conventional methodologies is discussed below. A more detailed review of conventional methods for predictive solubility determination can be found in *Aqueous Solubility: Methods of Estimation for Organic Compounds*; Yalkowsky and Banerjee; Dekker, New York (1992).

Some conventional methods for solubility prediction are based upon semi-empirical molecular orbital or quantum calculations. These approaches generally utilize complex 3-dimensional (3D) molecular descriptors to represent structural features with electronic properties such as atomic charges computed using molecular orbital calculations. A limitation encountered when using these types of methods is that they are generally directed towards the prediction of the solubility for small organic compounds and may not be suitable for solubility prediction for larger or more complex compounds such as drugs. Additionally, these approaches may involve solving quantum-based calculations that are computationally-intensive tasks that may not be suitable for rapid analysis of large numbers of molecules. Other conventional approaches require consideration of numerous molecular properties when performing the analysis to reproduce experimentally determined solubilities and may be limited to development of solubility models only when there is sufficient previously identified physiochemical property information.

Other conventional approaches to solubility prediction incorporate neural network modeling and Monte Carlo based simulation approaches. Typically, conventional models utilize numerous adjustable weighted variables and parameters that may lead to undesirably complex equations thereby reducing the speed with which solubility analysis may be performed. Like other conventional methods, Monte Carlo based modeling approaches may require 3D molecular structure information thus limiting their utility in analysis of large data sets and mining of extensive collections of compounds.

From the foregoing it will be appreciated that there is a need for an improved method for predictive solubility determination. In one aspect, it is desirable for such a method to be reasonably accurate and capable of rapid analysis even for large data sets. Moreover, it is desirable for the analysis methodology to incorporate a reduced number of descriptors or parameters so as to facilitate analysis and improve computational performance.

SUMMARY OF THE INVENTION

The present teachings describe a solubility prediction methodology that is based, in part, upon quantitative-structure property relationships (QSPR). In various embodiments, solubility prediction performance may be improved by identifying a reduced descriptor set comprising intuitive parameters that facilitate more rapid analysis as compared to other conventional methods that require 3-dimensional descriptors. The nature of the descriptors of the present teachings further facilitate virtual drug library design and optimization as researchers may better be able to ascribe meaning and/or significance to the descriptors as compared to the often arcane or complex descriptor constructions utilized by conventional methodologies. Moreover, in various embodiments, the present teachings provide solubility prediction relationships that may be resolved in a rapid manner to facilitate data mining and in silico screening of large libraries or collections of compounds. In various embodiments, the solubility prediction methods of the present teachings maintain a high degree of correlation with actual compound solubilities therefore reducing the requirement for experimental solubility determination or verification.

In one aspect, a novel descriptor association is disclosed as being proportional to the product of the number of hydrogen bond donors (HBD) and hydrogen bond acceptors (HBA). This parameter may reflect intermolecular hydrogen bonding between solute molecules and may be desirably used to represent solid-state cohesive energy or crystal packing forces affecting compound solubility.

In another aspect, the solubility analysis may utilize descriptors evaluated by regression analysis to identify linear equations that may be used to predict solubility for one or more compound classes or drug candidates. Use of the disclosed solubility model does not necessitate the determination of 3D structures or 3D descriptors for screened compounds. Instead, two-dimensional (2D) structure information and reduced numbers of data parameters or descriptors may be used as input for solubility determination. Subsequent descriptor analysis is performed in an efficient and rapid manner that facilitates solubility profiling for large numbers of compounds.

In another aspect, the invention comprises a method for solubility determination of at least one candidate compound by the steps of: Identifying a plurality of descriptors forming an initial descriptor set wherein each descriptor relates to a property of the candidate compound; Performing a correlation analysis to identify a plurality of substantially correlated descriptors within the initial descriptor set; Forming a reduced descriptor set from the initial descriptor set wherein selected correlated descriptors are retained from the plurality of substantially correlated descriptors; Identifying solubility information and descriptor values associated with the reduced descriptor set for a plurality of known compounds forming a training data set; Identifying a solubility equation based on a selected subset of descriptors contained in the reduced descriptor set and derived using the solubility information and descriptor values for the plurality of known compounds contained in the training data set; and Applying the solubility equation to the descriptor information for the at least one candidate compound to thereby determine the solubility for the at least one candidate compound.

In still another aspect, the invention comprises a method for solubility prediction comprising the steps of: Selecting a first plurality of descriptors comprising identifiable compound properties and characteristics; Forming a correlated descriptor subset from the first plurality of descriptors wherein the correlated descriptor subset comprises selected descriptors identified by correlation analysis; Generating a solubility prediction function comprising selected descriptors from the correlated descriptor subset identified by statistical analysis of the correlated descriptor subset using a training data set; and Applying the solubility prediction function to predict a compound's solubility on the basis of descriptor information for the compound.

In yet another aspect, the invention comprises a method for descriptor construction to be used in solubility analysis applications, comprising the steps of: Selecting a compound or molecular structure; Determining the number of hydrogen bond donors <HBD> in the selected compound or molecular structure; Determining the number of hydrogen bond acceptors <HBA> in the selected compound or molecular structure; Determining the product of the number of hydrogen bond donors and the number of hydrogen bond acceptors <HBD>*<HBA>; and Associating the product of the number of hydrogen bond donors and the number of hydrogen bond acceptors <HBD>*<HBA> with a first solubility descriptor for the selected compound or molecular structure.

In another aspect, the invention comprises a system for assessing the solubility of at least one compound, the system comprising: A descriptor identification component that identifies a plurality of descriptors describing properties and characteristics for the at least one compound; A correlation analysis component that evaluates correlations between the plurality of descriptors to identify correlated descriptor groups and further identifies at least one selected descriptor to represent one or more of the correlated descriptor groups; and A solubility modeling component that uses the at least one selected descriptor to form a solubility prediction equation using a training data set for which solubility and selected descriptor information is known.

In yet another aspect, the invention comprises a method of predicting the solubility of a compound in a solvent, comprising the steps of: Counting the number of hydrogen bond donors in each molecule of said compound; Counting the number of hydrogen bond acceptors in each molecule of said compound; Multiplying said counts to produce a descriptor value; Multiplying said descriptor value by a scaling factor to produce a first term of an equation; and Adding said term to other terms of said equation to produce a predicted solubility value.

In still another aspect, the invention comprises a computer readable medium having stored thereon instructions which cause a general purpose computer to perform a method of generating a predicted solubility value for a selected compound, said method comprising the steps of: Counting the number of hydrogen bond donors in each molecule of said compound; Counting the number of hydrogen bond acceptors in each molecule of said compound; Multiplying said counts to produce a descriptor value; Multiplying said descriptor value by a constant to produce a first term of an equation; and Adding said term to other terms of said equation.

BRIEF DESCRIPTION OF THE DRAWINGS

FIG. 2 illustrates a solubility regression analysis method,

DETAILED DESCRIPTION OF THE PREFERRED EMBODIMENT

Figure 1:
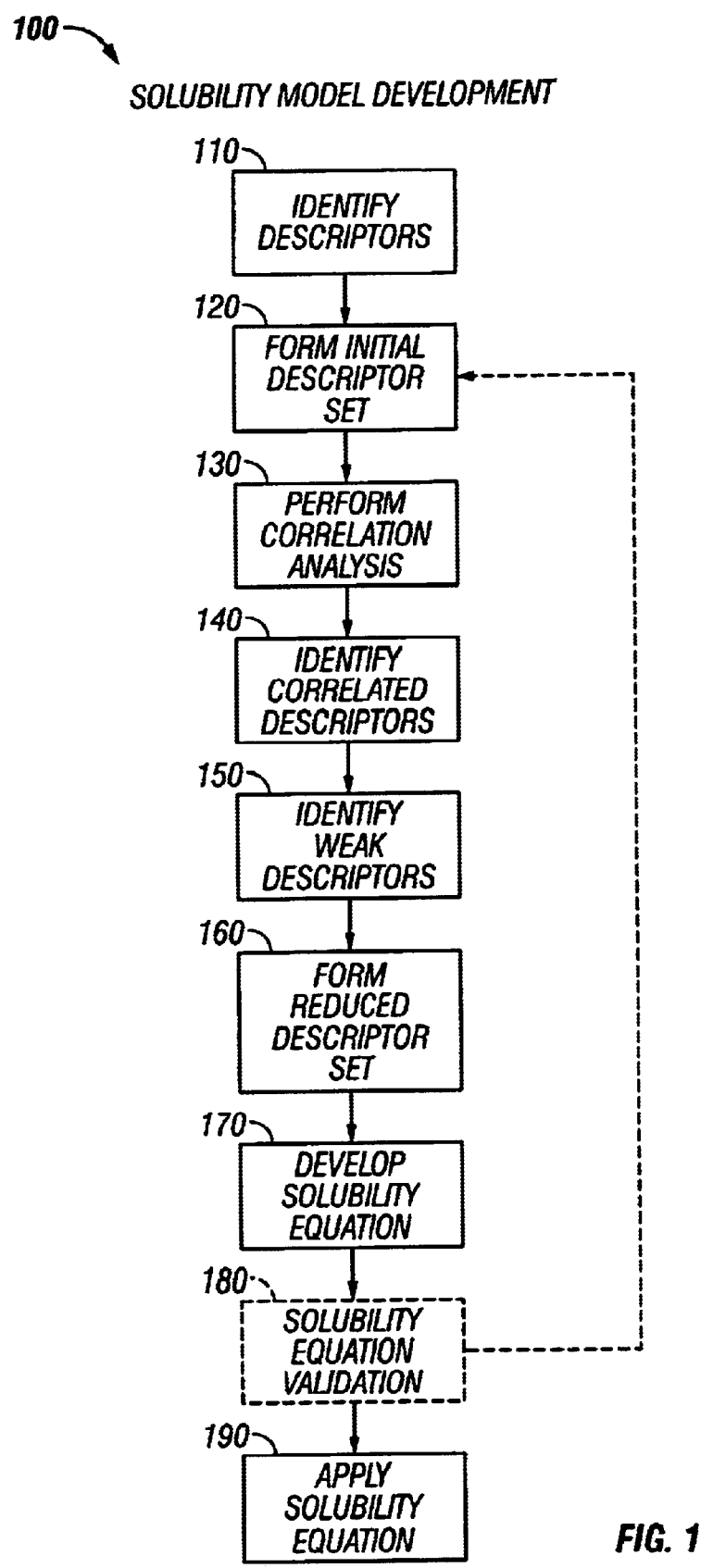
FIG. 1 illustrates a method for predictive solubility equation development.

When profiling large collections of synthesized and virtual libraries of compounds, fast analysis methods may be advantageously employed to screen for compounds having desirable characteristics/properties. The solubility of a compound is one such property that is often evaluated when considering the potential utility of a pharmacological agent or drug.

In one aspect, the solubility of a compound may be defined as the amount of solute dissolved in a saturate solution under an equilibrium condition. For example, the solubility of a compound may be measured as the amount of that compound that will dissolve in a solvent, such as water or blood, at a specified temperature. Solubility determination is particularly important in many areas of research and may be relevant to pharmacokinetic properties including absorption, distribution, metabolism, excretion and toxicity. Appropriate physiochemical properties together with the aforementioned pharmacokinetic properties and toxicity are often considered principle determinants for identifying useful drug candidates.

In one aspect, early identification of drug candidates which possess undesirable solubility characteristics may be advantageously used to "screen-out" those compounds which would not be suitable for medicinal purposes. Compound screening in this manner may reduce costs associated with drug discovery by removing undesirable compounds early in the drug discovery lifecycle. In another aspect, predictive solubility models and methodologies are important to identify and prioritize drug candidates for further development. Furthermore, solubility analysis may be used to assist in the rational design of compounds with desirable solubility profiles and to direct the development of experimental studies and animal tests.

In various embodiments, the present teachings address the need for predictive solubility modeling and determination by providing a method for rapid solubility analysis based, in part, upon a quantitative structure-property relationship (QSPR) model that predicts equilibrium aqueous solubility (e.g. 298K/unbuffered aqueous solution) from the molecular structures of one or more compounds. It will be appreciated however, that the methods described herein may be applied to numerous different physical conditions (e.g. different temperatures, pressures, pH ranges, etc.) and furthermore may be adapted to different solution compositions (e.g. blood, mixed-compound solutions, organic, and inorganic solutions).

In various embodiments, the QSPR model for predicative solubility determination utilizes linear regression analysis and genetic algorithm approaches for identifying solubility equations that may be used to predict the solubility of one or more selected compounds. A wide variety of different types and classes of compounds may be assessed using this approach including small organic and inorganic molecules, drugs, and drug-like species. In one aspect, solubility prediction may include evaluation of how the presence of one or more functional groups may affect the solubility for selected compounds.

Furthermore, training data sets, comprising actual or experimentally determined chemical/physical property information for a plurality of compounds, may be used to assess the predicted solubility results obtained from the solubility equations. In one aspect this assessment may comprise determining the degree of agreement between training data set solubilities versus predicted solubilities for one or more selected compounds using the methods described herein. The use of diverse training sets may therefore be used to improve the accuracy of solubility prediction across a wide range of different drug compositions.

FIG. 1 illustrates an exemplary method 100 for predictive solubility determination. In one aspect, the method 100 may be used to predict solubility for numerous different types/classes of compounds for which little or no existing experimental information exists. Furthermore, this method 100 may be advantageously utilized in connection with both real and simulated compounds to provide solubility information which may accurately reflect the true solubility of the compound under various experimental conditions.

The method 100 commences in state 110 with the identification of descriptors that are available for one or more compounds or molecules whose solubility is to be desirably determined. In one aspect, each descriptor comprises a calculable property of the compounds or molecules that may serve as numerical descriptions or characterizations in subsequent calculations. As will be described in greater detail herein below, the principle of descriptor identification advantageously facilitates the formation of a solubility equation that can be used to predict the solubility of the compounds or molecules using only descriptor-based information.

Numerous descriptors have been described for use in molecular modeling applications. In one aspect, descriptors can be broadly subdivided in categories including 2D and 3D descriptors and other physical/chemical properties. Briefly described, 2D descriptors may be generally associated with molecular or atomic composition, structural data, and/or atomic bonding information. This information may include numerous different characterizations and classifications for each compound including, for example: topological connectivity and electro-topological indices.

Furthermore, 3D descriptors may include information about the compounds including, for example, 3D coordinate information, spatial conformations, rotational information, translations of conformation, molecular/receptor docking information, and other properties based on the 3D structural information. As described above, 3D descriptor information is typically complex in nature and use of this type of information may substantially increase the computational time required to solve solubility determination equations.

In various embodiments, the present teachings desirably reduce the complexity associated with solubility prediction by reducing or eliminating the incorporation of complex 3D descriptor information. Although these types of descriptors may be readily integrated into the solubility determination process, construction of solubility equations in the manner described by the present teachings tend to produce results of substantially comparable accuracy as may be obtained when incorporating more complex 3D descriptor information while advantageously reducing computational overhead.

In one aspect, the descriptors identified in state 110 may comprise numerous types or classes of descriptors obtained from molecular modeling or simulation applications. One such application comprises the Cerius$^2$ (Accelrys, San Diego Calif.) modeling and simulation environment. Briefly described, this application provides that ability to identify candidate descriptors through molecular structure modeling of the selected compounds. In one aspect, the models are formed by identifying quantitative structure property relationships that may be translated into descriptors for use in solubility determination. These descriptors may include numerous descriptor types including structural, topological, electronic and spatial parameters. Furthermore, the aforementioned 2D and 3D descriptors may be determined using this modeling environment. Additional information detailing the features and operation of the Cerius$^2$ modeling and simulation environment may be found in http://www.accelrys.com/cerius2/index.html which is hereby incorporated by reference in its entirety.

Following descriptor identification in state 110 an initial descriptor set may be formed in state 120. In one aspect, the initial descriptor set comprises a plurality of descriptors which may include some or all of the aforementioned descriptors in addition to other descriptors. Upon identifying the initial descriptor set, the method 100 proceeds to state 130 where a correlation analysis is performed. In one aspect, the correlation analysis desirably evaluates each of the descriptors contained within the initial descriptor set to identify substantially correlated descriptors. Substantially correlated descriptors reflect two or more descriptors whose behavior or characteristics appear to possess a degree of statistical association where changes in one substantially correlated descriptor may be associated with predictable changes in another substantially correlated descriptor. Therefore, from a group of substantially correlated descriptors a single correlated descriptor is selected for use in subsequent solubility model development. Selection in this manner provides a means to reduce the total number of descriptors while advantageously avoiding selecting multiple descriptors that have been determined to be statistically correlated.

In one aspect, selecting a large number of statistically correlated descriptors for solubility model development may be less desirable as compared to selecting a lesser number of descriptors with a reduced statistical correlation. Using a large number of descriptors may lead to overfitting of the training set. In selecting descriptors with reduced statistical correlation a more robust solubility model may be generated. Furthermore, the solubility model provided by selecting a lesser number of descriptors oftentimes may aid in simplifying calculations associated with solubility prediction and therefore may improve the speed with which the analysis may be performed.

One manner by which the correlation analysis in state 130 may be performed comprises identifying pair-wise correlation coefficients between each of the descriptors contained within the initial descriptor set. Using this approach, descriptors that are determined to be substantially correlated to one another may be grouped together and from this group a reduced number of descriptors may be selected. In various embodiments, the number of descriptors selected from the substantially correlated group may be as few as one.

In one aspect, a threshold correlation coefficient may be selected to assess the correlation of a group of descriptors. The threshold correlation coefficient may further be selected to reside substantially between 0.8 and 1.0 indicating a relatively high degree of correlation between grouped descriptors. While the aforementioned range has been found to function well as the threshold, it will be appreciated that more or less selective thresholds may be readily used.

Subsequently, in state 150 the solubility model development 100 may proceed by identifying any weak descriptors. In one aspect, weak descriptors may be characterized as descriptors that may be useful for analyzing relatively few classes of compounds while being of little or no utility in evaluating other compound classes. Weak descriptors of this type may be desirably removed from subsequent solubility analysis as they may not be broadly applicable to solubility analysis for diverse classes of compounds and thus may unduly complicate any resultant solubility equations. In another aspect, removal of weak descriptors advantageously improves the quality of solubility prediction for a wider variety of potential compounds and thus helps to provide a solubility equation with improved versatility.

Following descriptor correlation and weak descriptor removal, the method 100 proceeds to state 160 where a reduced descriptor set is identified. The reduced descriptor set comprises selected correlated descriptors from the one or more substantially correlated descriptor groups identified in state 140 along with any additional descriptors that are to be desirably included in subsequent analysis. In one aspect, the reduced descriptor set serves as the principle input information for solubility equation development in state 170. Additional details of an exemplary reduced descriptor set will be discussed in greater detail hereinbelow with reference to Table 2.

In various embodiments, the solubility model may be characterized by an equation that incorporates one or more of the descriptors contained within the reduced descriptor set. In developing the solubility equation, it is often desirable to further reduce the number of descriptors required for analysis while preserving those descriptors that substantially contribute to accurate solubility prediction. In one aspect, a plurality of solubility equations may be identified based on various combinations of descriptors selected from the reduced descriptor set which may be used to predict solubilities for one or more selected compounds. From these equations, it is desirable to select the equation which provides a good combination of descriptors while maintaining an equation of reduced complexity.

When selecting the descriptors to be included in the solubility equation it is further desirable to select descriptors that are physically intuitive. Selection of descriptors in this manner facilitates researcher understanding of the solubility equation and reduces the often arcane complexity of solubility prediction equations provided by conventional methods. In one aspect, the intuitive nature of the descriptors incorporated in the solubility equation advantageously facilitates subsequent researcher development and refinement of the solubility equation.

In one aspect, development of the solubility equation in state 170 may be accomplished using several statistical analysis approaches. As will be described in greater detail hereinbelow statistical analysis comprises identifying one or more possible solubility equations that are analyzed to determine a statistically significant group of descriptors to be used in the final solubility equation. Typically, the final solubility equation comprises a combination of those descriptors that are determined to possess a high degree of statistical significance. While linear regression analysis provides a convenient and reliable method for determining the solubility equation, it will be appreciated that other approaches may be used to evaluate the reduced descriptor set and identify the solubility equation. In various embodiments, statistical techniques including: genetic algorithm approximation, partial least squares approximation, and stepwise regression approaches may also be used to achieve a similar result as the regression analysis.

Upon identifying the solubility equation in state 170, the method 100 may proceed to validate the solubility equation in state 180. In one aspect, solubility validation comprises identifying one or more validation data sets each of which may be comprised of a plurality of compounds and/or molecules with known solubilities and descriptor information. Using the descriptor information from the validation data sets, the solubility equation may be used to predict the solubility for each compound in the validation data set. The predicted solubility results may then be compared to the actual or known solubility values to determine the accuracy and performance of the solubility equation.

In one aspect, solubility equation validation flyer serves as a means to refine the solubility equation where those descriptors used in the solubility equation may be reintroduced as a new initial descriptor set in state 120. Thereafter, the solubility model development method 100 may operate as previously described to further reduce the number of descriptors used in a subsequent refined solubility equation. Thereafter, the identified solubility equations may be assessed using the validation data set information to determine if acceptable results are achieved using the refined solubility equation as compared to the initial solubility equation. By performing iterative refinement in this manner, additional descriptors may be removed from the initial solubility equation to further increase the simplicity and efficiency with which solubilities may be predicted. As will be appreciated by one of skill in the art, the iterative process of solubility equation refinement may be performed as desired any number of times.

Finally, in state 190 the solubility equation may be applied to predict solubilities for one or more known and/or unknown compounds or molecules. As previously indicated the solubility equation is useful in predicting solubilities for both real and virtual compounds and may be implemented in high-throughput solubility predication applications with large libraries or collections of compounds of interest.

FIG. 2 illustrates one embodiment of a method 200 for performing the aforementioned statistical analysis to determine a solubility equation based upon quantitative structure property relationships (QSPR). The method 200 commences in state 210 where a particular statistical method is selected for analyzing the descriptors contained within the descriptors set. While a number of approaches may be used for descriptor analysis, it is important to select a method that can efficiently evaluate a potentially large and diverse number of descriptor types and combinations.

One particular method for analysis that has been found to be suitable for statistical evaluation of a wide range of descriptors comprises a modified partial least squares approach that integrates genetic algorithmic evaluation (G/PLS). Use of the G/PLS methodology is desirable in applications including descriptor evaluation as this approach is able to identify statistically significant descriptor combinations that are suitably accurate in terms of predicting solubilities. Additional information detailing the features and operation of the G/PLS regression analysis methodology may be found in Genetic Algorithms in Molecular modeling, pp 109–130 (1996), "Genetic partial least Squares in QSAR", Ed. J. Deviilers, Academic Press, London, England, which is hereby incorporated by reference in its entirety.

In state 220, the selected statistical methodology is applied to the descriptors contained in the reduced descriptor set to develop one or more candidate solubility equations. In one aspect, there may be several candidate solubility equations that provide similar accuracy or desirable numbers of descriptors. From these candidate solubility equations, a final solubility equation is desirably identified that appears to contain the most statistically significant collection of descriptors.

In another embodiment, a second statistical methodology may be used to supplement or confirm the results provided by the first selected statistical methodology. For example, a stepwise regression method may be applied to the descriptor set to augment and confirm the results obtained using the G/PLS regression method. In this manner multiple linear regressions may be used to construct the final solubility equation thereby improving the confidence and degree of accuracy for solubility prediction.

In one exemplary approach, the number of descriptors to be included in the solubility equation is determined by a regression approach using increasing numbers of descriptors while assessing both a coefficient of determination $R^2$ and a leave-one-out $R^2$ value in state 230. In one aspect, assessment of the coefficient of determination $R^2$ value is desirable as this value generally improves as the number of descriptors is increased. However, cross-validated $R^2$ values may generally increase initially and then begin to decline as the number of descriptors increase. The point substantially at which the cross-validated $R^2$ values begin to decline may be indicative of over-fitting and suggest that further increases in the descriptor number may not improve the regression analysis significantly. Thus, by assessing the $R^2$ values a suitable number of descriptors may be included in the solubility equation while avoiding incorporating an excessive descriptor number which might otherwise degrade the quality of the predictive analysis.

The final statistical model is used to define the solubility equation in state 240. In various embodiments, the solubility equation may be characterized by a substantially linear model having approximately 4–12 descriptors. The actual number of descriptors used for a particular solubility equation varies, however, and it will be appreciated that the solubility equation may contain more or less descriptors than that indicated by the aforementioned range. One desirable benefit of solubility equation formation in this manner is that relatively accurate solubility equations may be determined that do not require the use of 3D structure information or 3D descriptors to accurately predict the solubility of compounds of interest.

As previously indicated the resulting solubility equation identified in state 240 may then be used to predict solubilities for a plurality of compounds contained in one or more validation data sets. Comparing the predicted solubilities for these known compounds to the predicted solubilities provides a means to validate the solubility equation. Furthermore, if it is observed that there are tendencies or trends amounting to inaccuracies in solubility prediction. Then the solubility equation can be re-evaluating using the aforementioned methods in combination with additional/different descriptors to provide improved results.

The following description and associated Figures and Tables provide an exemplary application of the solubility determination approach to identify significant descriptors and an associated solubility equation. It will be appreciated that this discussion of the various data, information, parameters, and descriptors represents but one embodiment of the process and that in various embodiments modifications, changes, and/or substitutions may be made to construct other solubility equations which may be applicable to other data sets.

Figure 3A:
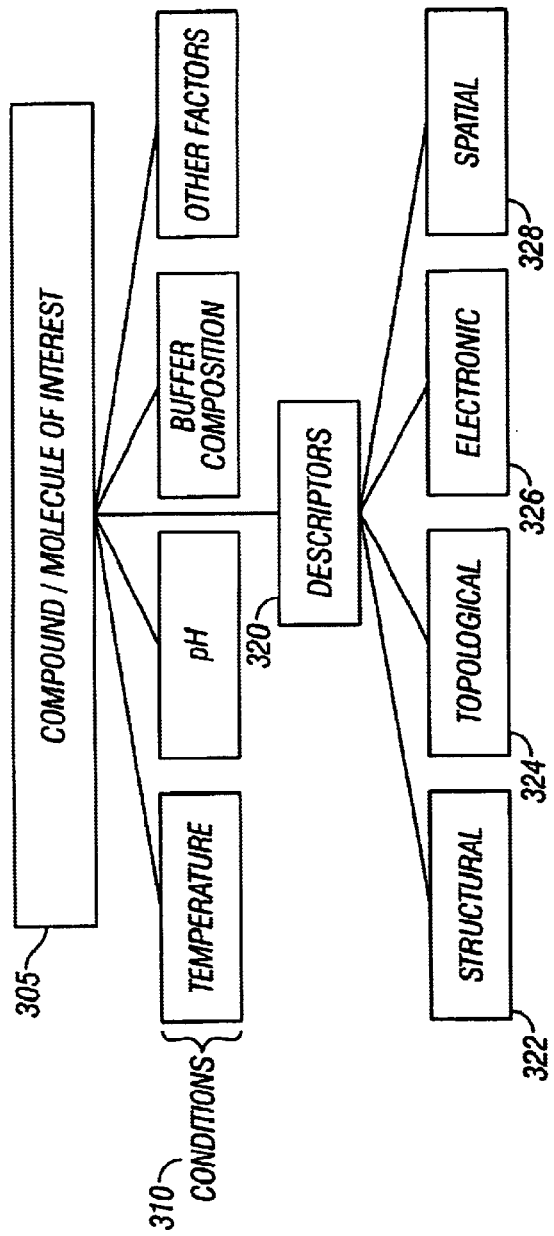
FIG. 3A is a block diagram illustrating various compound characteristics for solubility determination.

FIG. 3A illustrates some exemplary considerations for compounds and/or molecules 305 that may be useful in descriptor determination and subsequent solubility equation identification. In one aspect, solubility prediction for one or more compounds 305 may include consideration of the physical/chemical conditions or environmental variables 310 in which the compounds 305 will be desirably modeled within. These environmental variables 310 may include temperature, pH, buffer composition, and other factors which affect the solubility of the compound 305. As previously indicated, prediction of the solubility of the compound 305 may be modeled using a static condition set which is applied to the QSPR model. In one aspect, by limiting conditions to a non-variable state, complex physical processes, such as solubility determination, can be more effectively modeled using the QSPR model to simplify the calculations needed to predict the compound solubility. For example, in one static condition set, solubility prediction analysis of the compounds 305 may be conducted at temperature of approximately 298 K in an unbuffered aqueous solution with a pH dependent upon the nature and composition of the compound 305.

Furthermore, a plurality of descriptors 320 may be identified as potentially relevant to the solubility prediction. In one aspect, numerous descriptors 320 are available for subsequent consideration and analysis. These descriptors 320 are desirably selected from a wide range of physical and chemical properties for the compounds 305 and may include descriptors describing structural 322, topological 324, electronic 326 and spatial 328 parameters. Analysis of these descriptors 320 may be further correlated with one another according to the regression methodology described above.

Figure 3B:
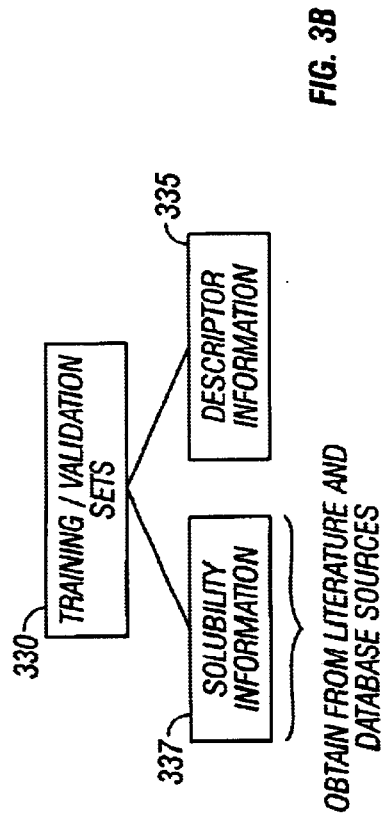
FIG. 3B is a block diagram illustrating the composition of a training/validation data set.

As shown in FIG. 3B, model development may be facilitated by the formation of one or more training or validation data sets 330 containing compounds or molecules with known descriptors 335 and solubility information 337. This solubility information may be acquired from numerous sources including literature references (e.g. scientific papers, publications, and reference books). Other sources for compound information include the Physicians Desk Reference (PDR), the Merck Index, the Handbook of Chemistry and Physics, and/or other such collections of chemical information.

Furthermore, descriptor and solubility information may be acquired from both public and private database sources of compound information. Database sources of compound information may comprise solubility information and other information for compounds which have been stored in both electronic and non-electronic formats. One example of an electronic database from which solubility information may be acquired comprises the AQUASOL dATAbASE of Aqueous Solubility described in detail by Yalkowsky. This database contains nearly twenty thousand solubility records representative of close to six thousand compounds. The information contained in this database further includes solubility data for a wide variety of compounds, including many pharmaceuticals, pollutants, nutrients, herbicides, pesticides, agricultural, industrial, and energy related compounds.

In various embodiments, the solubility information obtained by inclusion of the literature and database sources of information provide a source of known solubility values useful in assessing the initial quality and accuracy of the predictive model by comparing the results of the solubility equation with expected solubility values. Furthermore, these sources of solubility information provide a large collection of similar and disparate compositions which are useful in creating solubility models capable of assessing solubility characteristics over a wide range and variety of compound types.

In one aspect, the training/validation data sets 330 may comprise as many as several hundred compounds or more that may be identified for the purposes of testing and refining the solubility equation. The data sets 330 may include both small and large molecules and furthermore may desirably include numerous functional groups. Additionally, molecules containing multiple functional groups may be included in the data sets 330. Further details of exemplary functional groups that may be considered during solubility analysis will be discussed in greater detail hereinbelow with reference to Table 1.

Figure 4A:
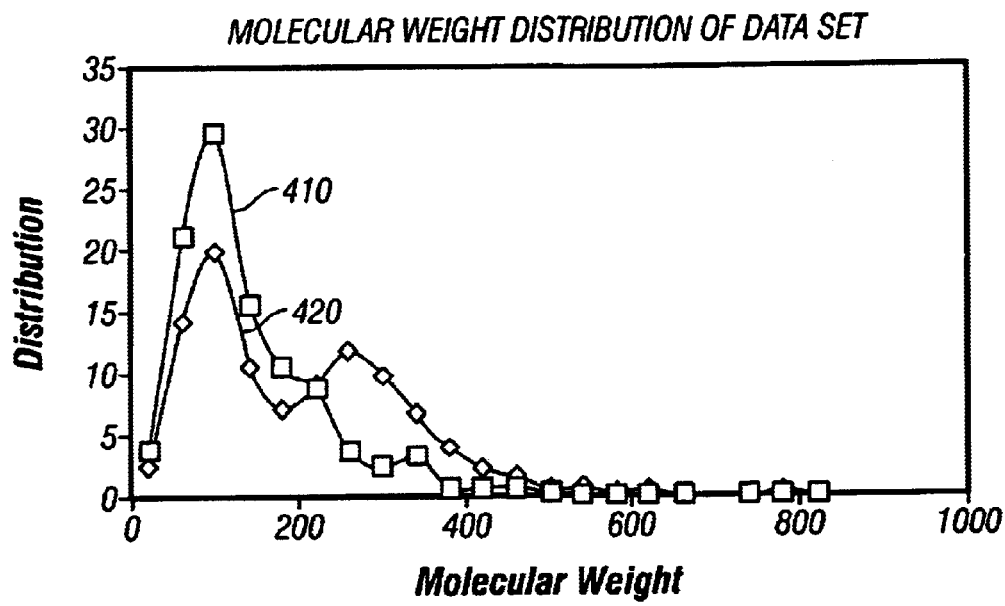
FIG. 4A is a graph illustrating the molecular weight distribution for two exemplary data sets.

FIG. 4A illustrates exemplary molecular weight distribution characteristics 400 for two selected data sets 410, 420 that may be used in a solubility equation determination and validation according to the present teachings. In one aspect, a plurality of compounds having an approximate molecular weight similar to candidate compounds of interest for which solubility will be predicted are desirably identified. As shown in the illustration, different molecular weight distributions may be selected for the one or more data sets to be used in conjunction with the solubility equation modeling process. For example, the exemplary first data set 410 may comprise a high percentage of compounds with a molecular weight in the range of approximately 0–400 with a lesser number of compounds residing in the molecular weight range of 400–1000. In a similar manner the exemplary second data set 420 may comprise a more even distribution of compounds in the molecular weight range of 0–500 with a lesser number of compounds in the molecular weight range of 500–1000. In one aspect, the experimenting with multiple training sets 410, 420 desirably demonstrates how to improve the quality and accuracy of the solubility equation and provide a means to validate its performance. It will be appreciated that the composition of the data sets may be selected to accommodate a wide variety of compounds which may be representative of particular classes of functional groups or possess desirable distributions of characteristics similar to that for which solubility will be predicted.

Figure 4B:
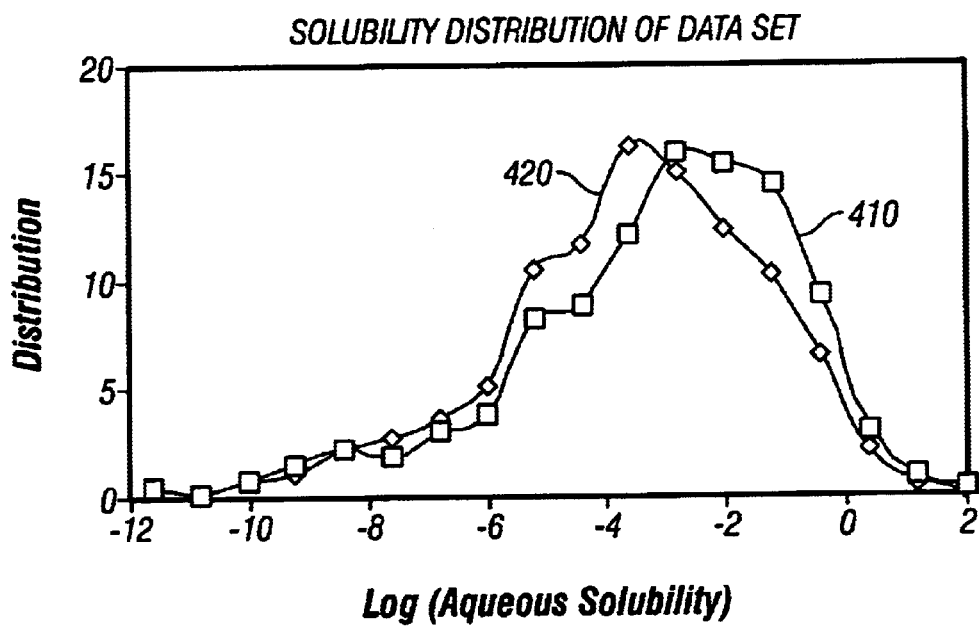
FIG. 4B is a graph illustrating the solubility distribution for two sets.

FIG. 4B illustrates a logarithmic plot of the aqueous solubility, in moles/liter, for the exemplary data sets 410, 420. The distribution of the solubilities 370 of the two data sets 410, 420 may be similar or disparate in composition. Each data set 410, 420 may further comprise a plurality of compounds with varied solubilities that may be similar to, or anticipated for compounds of interest whose solubility is to be predicted using the solubility equation. In one aspect, a greater distribution of compounds with a solubility substantially within a selected range are desirably identified to aid in validating and promoting increased accuracy of the solubility equation for one or more selected classes of compounds. For example, it may be desirable to generate a solubility equation that is highly accurate for a specified range of solubilities associated with a selected class of drug-candidate characteristics or profiles. The data sets 410, 420 may therefore be configured to reflect the specified range of solubilities in detail while providing additional solubility information for compounds that reside outside of the desired solubility range. Taken together, the distribution of solubilities in the selected data sets may provide highly accurate solubility prediction within the specified solubility range while still providing acceptable accuracy for compounds which reside outside of the specified solubility range. In one aspect, selection of solubility ranges is useful in ranking drug candidates or compounds of pharmaceutical interest according to potential utility. Additional details of this ranking methodology will be described in greater detail with reference to Table 5 and FIG. 7 below.

TABLE 1

| Functionality |
| --- |
| Alkanes |
| Alkenes |
| Alkynes |
| Halogen derivatives |
| Aromatic and cyclic |
| N-containing compounds: Nitros, Nitriles, Amides |
| Amines |
| Alcohols |
| Ketones |
| Aldehydes |
| Esters |
| Ethers |
| Acids |

Table 1 illustrates exemplary functional groups that may be included in the training/validation data set and may be considered during solubility prediction. In one aspect, the compounds to be selected for use in the data set may comprise organic compounds and molecules which desirably posses one or more associated functional groups. Functional group evaluation may further represent a significant factor in solubility prediction as each functional group may affect the actual/predicted solubility of the compound. As indicated in Table 1, exemplary functional groups that may be considered in conjunction with the various compounds which form the data set include hydroxyls, alkanes, alkenes, alkynes, halogen derivative groups, aromatic and cyclic groups, nitrogen-containing groups (nitro, nitrile, amide), amines, alcohols, ketones, aldehydes, esters, ethers, acids, sulfur-containing groups, and other functional groups as are known to those of skill in the art.

It will be appreciated that the compounds to be included in the training/validation sets may be selected randomly or pre-selected on the basis of their physical properties including functional group composition. These physical properties may include molecular weight and/or solubility characteristics, as previously indicated. Additionally, separate training and validation data sets may be identified with the validation sets desirably kept separate from the training sets in order to allow monitoring of the performance or accuracy of the solubility equation for one or more selected compounds that were not used in the initial solubility equation formation process.

TABLE 2

| Descriptors | Definition |
| --- | --- |
| MW | Molecular weight |
| Rotlbonds | Number of rotable bonds |
| AlogP98 | Water-octanol partition coefficient calculated using Cerius2 AlogP98 model |
| Hbond donor | Number of hydrogen bond donors |
| Hbond acceptor | Number of hydrogen bond acceptors |
| HBD*HBA | The product of hydrogen bond donors and acceptors |
| Topological indices | |
| JX | Balaban index |
| PHI | Kier & Hall flexibility index |
| Zagreb | The sum of the squares of vertex velancies |
| Wiener | The sum of the chemical bonds existing between all pairs of heavy atoms in the molecules |
| Electrotopological indices (for atom types) | |
| S_sCH3 | CH3 group single bonded to any atom |
| S_dCH2 | CH2 group double bonded to any atom |
| S_ssCH2 | CH2 group bonded to any two atoms via single bonds |
| S_aaCH | CH group has two aromatic bonds attached to it |
| S_sssCH | CH group has 3 single bonds attached to it |
| S_dssC | A carbon atom has two single bonds and one double bond attached to it |
| S_aasC | A carbon atom has two aromatic and a single bond attached to it |
| S_ssssC | A carbon atom has four single bonds attached to it |
| S_aaaC | A carbon atom has three aromatic bonds attached to it |
| S_δNH2 | NH2 group single bonded to any atom |
| S_ssNH | NH group has two single bonds attached to it |
| S_dNH | NH2 group double bonded to any atom |
| S_dsN | A nitrogen atom has a single bond and a double bond attached to it |
| S_aaN | A nitrogen atom has two aromatic bonds attached to it |
| S_sssN | A nitrogen atom has three single bonds attached to it |
| S_dO | An oxygen atom double bonded to any atom |
| S_ssO | An oxygen atom has two single bonds attached to it |
| S_sOH | An OH group single bonded to any atom |

Table 2 illustrates an exemplary collection of descriptors that may be assessed for incorporation into the solubility equation. As previously described, the descriptors may be derived from different physical/chemical characteristics and may include general descriptors such as molecular weight and number of rotatable bonds within a selected compound as well as more complex descriptors obtained from topological indices and electro-topological indices. In one aspect, these descriptors comprise the subset of descriptors forming the reduced descriptor set from which the solubility equation is derived by regression analysis. It will be appreciated that the descriptors illustrated in Table 2 do not necessarily represent a comprehensive collection of descriptors and other descriptors may be included in the solubility equation analysis approach. Furthermore, each of the descriptors may be desirably associated with a numerical value which may be integrated into the solubility equation to thereby weight the contribution each descriptor makes to the solubility equation by a calculable factor.

Equation 1 illustrates one example how the descriptors may be integrated into the solubility equation that may be used to predict solubility for one or more compounds. In this equation, a reduced number of descriptors have been identified as being statistically relevant to solubility prediction and each descriptor has been multiplied by a numerical factor indicating its relative contribution to the predicted solubility.

$$\text{Log}(S_w) = Coeff_1 * \langle AlogP98 \rangle + Coeff_2 * \langle HBD \rangle * \langle HBA \rangle + Coeff_3 * \langle Zagreb \rangle + Coeff_4 * \langle S\_aaaC \rangle + Coeff_5 * \langle Rotlbonds \rangle + Coeff_6 * \langle HBD \rangle + Coeff_7 * \langle S\_sOH \rangle + Coeff_8 * \langle Wiener \rangle$$

Equation 1:

The solubility $S_w$ for a selected compound may be computed as a function of a relatively small number of descriptors. In one aspect, the solubility equation may be developed using one or more of the aforementioned training data sets. Each training data set is comprised of a plurality of molecules for which experimentally determined solubility information and descriptor information, such as that illustrated in Table 2, is available. Regression analysis using these descriptors may be carried out in a manner that will be described in greater detail hereinbelow to identify a substantially linear model that does not require 3D structure information. In one aspect, regression analysis advantageously produces a solubility equation that maintains a relatively high degree of statistical confidence while using only a limited number of relatively simple descriptors.

According to the solubility equation described by Equation 1, each descriptor indicated within brackets '<x>' may be represented by the mean-centered, unit-variance scaled value of each descriptor based on training set values and information. Furthermore, each descriptor may be associated with a scaling factor or coefficient 'Coeff'. In one aspect, the scaling factor is used to weight the contribution of the descriptor with respect to other descriptors in the solubility equation. According to the solubility equation each descriptor may be associated with a different scaling factor whose value may be positive or negative. Mean values for each descriptor may further be used in combination with calculated standard deviations for the descriptors to determine the scaling factor '$Coeff_{(1-8)}$' for each descriptor '<x>'.

In Equation 1 above, the <AlgoP98> descriptor is representative of the water-octanol partition coefficient calculated using the Cerius$^2$ Alog98 module. In one aspect this descriptor is a significant contributor to the solubility prediction equation and represents the hydrophobicity of a compound. In one aspect, the greater the value of the <AlogP98> descriptor, the more hydrophobic the compound may be thus decreasing its aqueous solubility.

Equation 1 further incorporates a novel composite descriptor construct comprising <HBD>*<HBA>. This descriptor is oftentimes a significant descriptor in predicting solubility and is comprised of the product of the <HBD> descriptor representing hydrogen bond donors and the <HBA> descriptor representing hydrogen bond acceptors. In various embodiments this descriptor construct may be reflect intermolecular hydrogen bonding between two solute molecules and the solid-state cohesive energy or crystal packing forces within the molecule. In general, increased intermolecular hydrogen bonding may be correlated with increased crystalline phase bonding between molecules, and hence, lower predicted solubility for a compound of interest.

In various embodiments, use of the composite descriptor <HBD>*<HBA> is significant in that it may provide an additional method by which to correlate descriptor information. For example, taken alone the <HBD> descriptor may be interpreted to reflect the hydrogen bonding capacity of a solute with water where increased hydrogen bonding capacity is indicative of increased predicted solubility. Thus the <HBD> descriptor taken alone may principally represent solute-solvent interactions. Conversely, when combined as the composite descriptor <HBD>*<HBA> solute—solute interactions may be modeled and incorporated into the solubility prediction equation as described above.

The <Zagreb> descriptor represents the sun of the square of the vertex valences for the molecule. The <Wiener> descriptor represents the sum of the chemical bonds between all pairs of heavy atoms (non hydrogen atoms) in the molecule. The <S_sOH> descriptor represents the summation of the electro-topological state values for the functional group type —OH in the molecule and the <S_aaaC> descriptor represents the summation of the aromatic carbon atoms in the molecule. Additional information describing each of these descriptors may be found in *J. Comput. Chem.*, 8, 170–173 (1987), "An Algorithm for Construction of the Molecular Distance Matrix", Bonchev, D., "Information Theoretic Indices for Characterization of Chemical Structures", Chemometrics Series, ed. D. D. Bawden, Vol 5, New York: Research Studies Press Ltd. (1983), and *J. Chem. Inf: Comput. Sci.*, 35, 1039–1045 (1995), "Electrotopological State indices for Atom Types: A novel Combination of Electronic, Topological and Valence State information", which are hereby incorporated by reference in its entirety.

Another example of a solubility equation generated according to the present teachings integrating the use of specific scaling factor values is described by the relationship:

$$\text{Log}(S_w) = -0.7325 * <AlogP98> - 0.4985 * <HBD> * <HBA> - 0.5172 * <Zagreb> + 0.0780 * <S\_aaaC> + 0.1596 * <Rotlbonds> + 0.2057 * <HBD)> + 0.1834 * <S\_sOH> + 0.2539 * <Wiener>$$ Equation 2:

It will be appreciated that the scaling factors associated with solubility equations generated according to the present teachings, including those illustrated in the aforementioned Equations, may be varied from one equation to another. In one aspect, the range of values for the scaling factor resides between approximately −1.0 and +1.0. A more precise value of the scaling factor may further be determined by analysis of the mean values for each descriptor along with their associated standard deviations as described above.

The aforementioned regression equations may be validated using compounds with known solubilities from the data sets 410, 420 to determine if the calculated or predicted results accurately represent the known solubilities for one or more of the compounds under study. Should errors or deviations from expected values be observed, for example, due to high molecular weight compounds outside of the molecular weight range of the current training data or due to compounds with multiple or different functional groups; additional training data sets may be generated and applied to the solubility analysis methods to improve the accuracy and confidence of the solubility equation.

Figure 5:
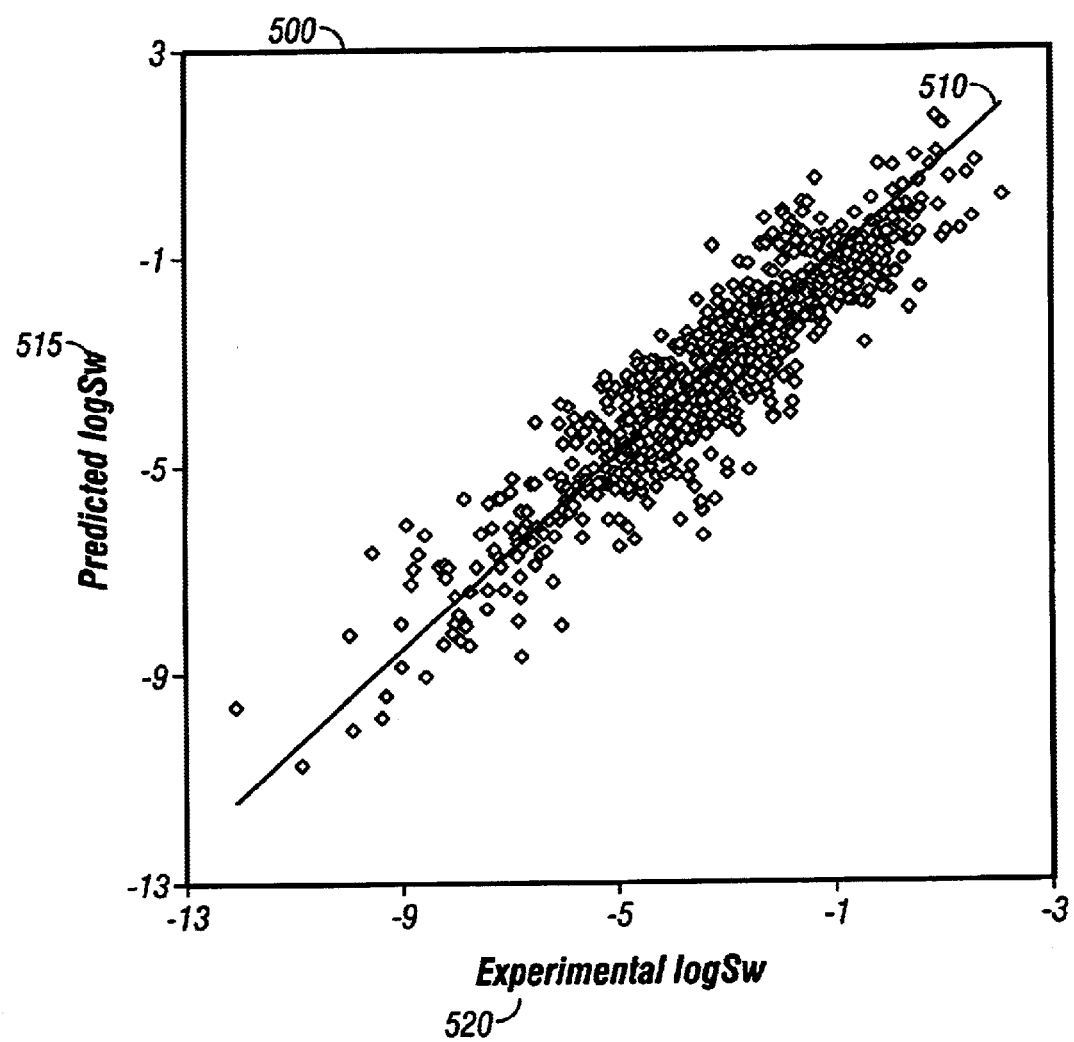
FIG. 5 is a graph comparing calculated versus actual solubilities for an set.

FIG. 5 illustrates an exemplary linearity assessment approach 500 used to analyze the solubility equations generated in accordance with the aforementioned methods. This approach 500 may be used to assess the relative accuracy of predicted solubilities 515 by comparison of the results against the experimentally obtained or known solubilities 520 for a plurality of compounds. Using an exemplary training data set comprising over seven hundred individual compounds, a relatively high correlation between predicted and experimental solubility may be observed when applying the exemplary solubility equation. In one aspect, the substantially linear trend 510 in data points indicates that the descriptors of the solubility equation may be useful in predicting solubilities for compounds of similar types as the training set. Furthermore, analysis of the solubility equation by comparison of training set data for predicted solubilities 515 versus known solubilities 520 may be useful in identifying when additional refinement of the solubility equation may be desirable. In this manner, the solubility equation can be "tuned" to further improve the training set correlation giving rise to a more accurate and reliable manner of solubility prediction.

The results of the linearity analysis 500 shown in FIG. 5 may also be analyzed by other statistical means such as significance probability assessment and analysis of variance. As shown in Table 3, each descriptor of the solubility equation may be evaluated to determine its significance in predicting solubility. In one aspect, determination of an F ratio value and significance of probability may be used to evaluate the significance of the descriptors. As will be appreciated by one of skill in the art, calculation of the F ratio value provides a test for the statistical significance of the observed differences among the means of two or more samples populations. Applying this test to the descriptors therefore provides a means to evaluate the relative significance of the descriptors in terms of solubility prediction. Additionally, this information may be used to rank or order the descriptors to identify those descriptors most highly correlated with accurate solubility prediction.

TABLE 3

| Descriptor | F ratio | Prob > F |
|---|---|---|
| <AlogP98> | 1332.23 | <0.0001 |
| <HBD>*<HBA> | 160.86 | <0.0001 |
| <HBD> | 42.69 | <0.0001 |
| <Rotlbonds> | 73.84 | <0.0001 |
| <Weiner> | 88.21 | <0.0001 |
| <Zagreb> | 370.4 | <0.0001 |
| <S_aaaC> | 23.35 | <0.0001 |
| <S_sOH> | 36.53 | <0.0001 |

For the exemplary descriptors illustrated in Table 3 evaluation of the F ratio value indicates that the <AlogP98> descriptor and <HBD>*<HBA> descriptor are statistically significant in terms of predicting solubility. Calculation of the significance probability further illustrates the significant of the descriptors as indicated by the relatively small value for each exemplary descriptor. Thus, using statistical methods similar to those described above, descriptors which lack sufficient significance may be identified and removed from the solubility equation, if desired, to potentially improve the accuracy of the regression equation. It will be appreciated that the aforementioned statistical analysis methods represent but one means by which to evaluate the significance of the descriptors and in other embodiments different statistical analysis methods may be readily used to perform similar functions.

TABLE 4

| Data set | Number of compounds | Signed error | Unsigned error | Root Mean Squared error |
|---|---|---|---|---|
| Training set | 775 | 0 | 0.68 | 0.87 |
| Small molecules | 34 | 0.17 | 0.64 | 0.62 |
| PDR | 61 | −0.28 | 0.8 | 0.95 |
| CMC | 166 | −0.02 | 0.95 | 1.15 |
| PHYSPROP | 1404 | −0.01 | 0.75 | 1.01 |

In one aspect, as shown in Table 4, the final solubility equation may be validated using one or more validation data sets. These data sets may desirably comprise diverse classes or categories of compounds. For example, in candidate drug discovery, useful validation data sets may include: a training data set used in solubility equation analysis, a data set comprising representative organic molecules, a data set comprising known drugs or medicinal compounds, a data set comprising drug-like compounds and a data set comprising a large and diverse collection of compounds from various literature and database sources. As shown by the exemplary analysis of signed error, unsigned error, and root mean squared error, the quality of the solubility prediction may vary from one data set to another. Like other methods for statistical analysis, these statistical treatments of the data sets may be useful in evaluating the performance of the solubility equation.

Figure 6:
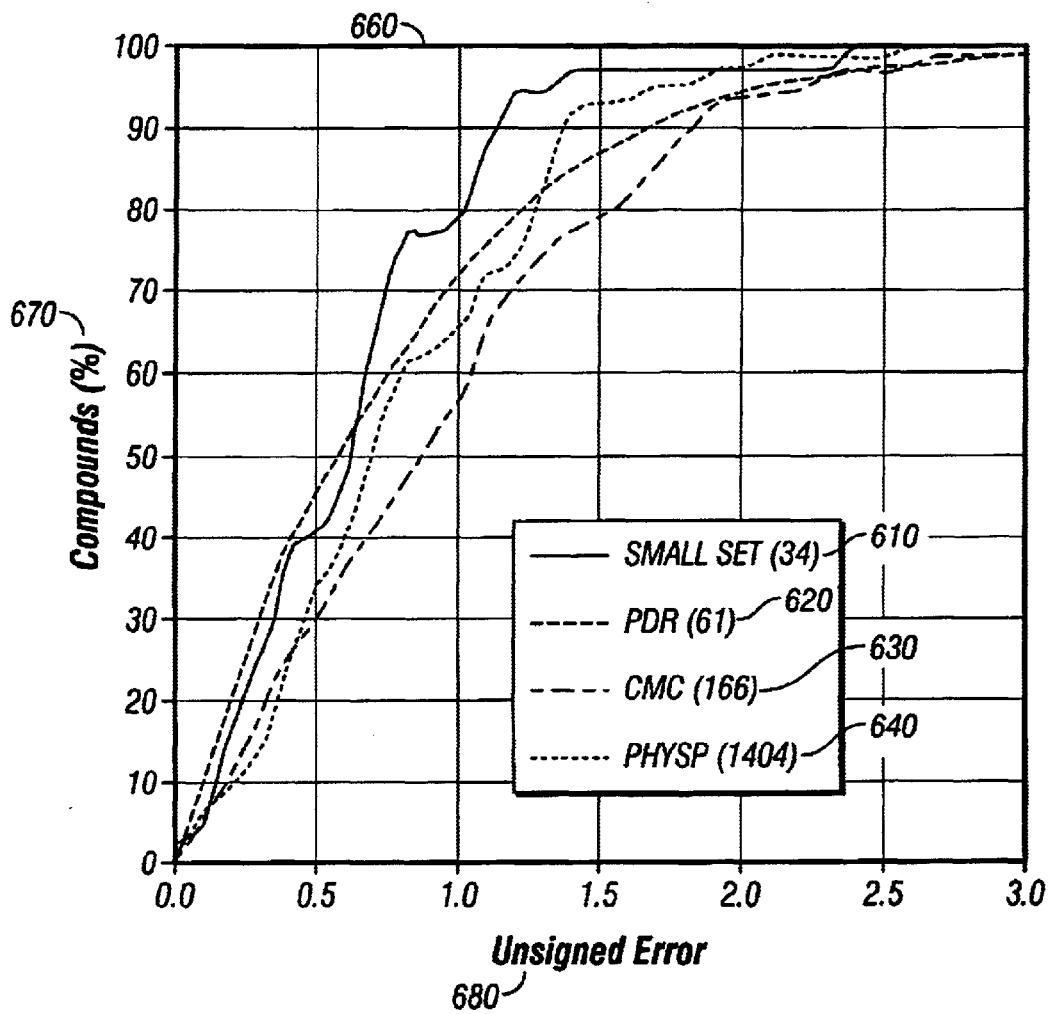
FIG. 6 is a graph illustrating the accuracy of solubility prediction for ry data sets.

FIG. 6 illustrates an exemplary graph 660 for the above-described data sets 610, 620, 630, and 640 in which the compound number 670 is plotted as a function of the deviation or unsigned error 680 of the predicted solubility from the experimental value. The graph 660 illustrates that for a tolerable error of 1 log unit, the solubility equation may correctly predict the solubility for as many as 60–80% of the selected compounds. For a tolerable error of 1.5 log units, the solubility equation can correctly predict the solubility for as many as 80–95% of the selected compounds. The information contained in this graph 660 illustrates but one example of the potential accuracy for prediction of solubility for a wide variety of compounds. It will be appreciated that other solubility equations are not limited by the accuracy's reflected in this graph 660 and may be more or less accurate. Graphing of the data in this manner, however, serves as a useful means to assess the relative effectiveness of the solubility equation in predicting solubilities for candidate compounds of interest.

TABLE 5

| Solubility Ranking | Solubility Range | Drug-likeness |
| --- | --- | --- |
| 0 | $\log(S_w) < -8$ | no, impossible |
| 1 | $-8 < \log(S_w) < -6$ | no, very low, but possible |
| 2 | $-6 < \log(S_w) < -4$ | yes, low |
| 3 | $-4 < \log(S_w) < -2$ | yes, good |
| 4 | $-2 < \log(S_w) < 0$ | yes, optimal |
| 5 | $0 < \log(S_w)$ | no, too soluble |

Table 5 illustrates an exemplary application of how the solubility prediction methods may be applied to data mining operations including compound and library design. In on aspect, evaluating the predicted solubility values for large number of compounds can be facilitated by construction of a ranking scheme. The ranking scheme may be used to identify or categorize groups of compounds with predicted solubilities within desirable ranges. These ranges may further be associated with a plurality of classifications or solubility categories indicative of the relative utility of the compound in future drug discovery based on its solubility. As previously indicated, the solubility of a compound may be an important consideration in establishing whether or not the compound is of likely utility in drug design applications. In one aspect, a useful drug candidate should desirably possess a balance between many physiochemical and pharmacokinetic properties including solubility.

Formation of the ranking scheme therefore advantageously allows a researcher to rapidly screen predicated solubilities by grouping together compounds with selected ranges of solubility. Thereafter, a particular solubility range may be selected and those compounds with solubilities which reside within the selected solubility range may be examined more closely or subjected to further drug discovery applications. In a similar manner, compounds which reside within an undesirable solubility range may be excluded from subsequent or drug discovery operations.

Application of the aforementioned solubility screening approach may therefore advantageously improve the efficiency of drug discovery and furthermore may reduce the time and cost associated with candidate drug selection by removing compounds which possess undesirable solubility characteristics early in the drug discovery lifecycle. It will be appreciated that the exemplified ranking scheme represents but one of many possible ranking systems that may be applied subsequent to solubility prediction and other ranking schemes based on solubility prediction may be readily devised without departing from the scope of the present teachings.

Figure 7:
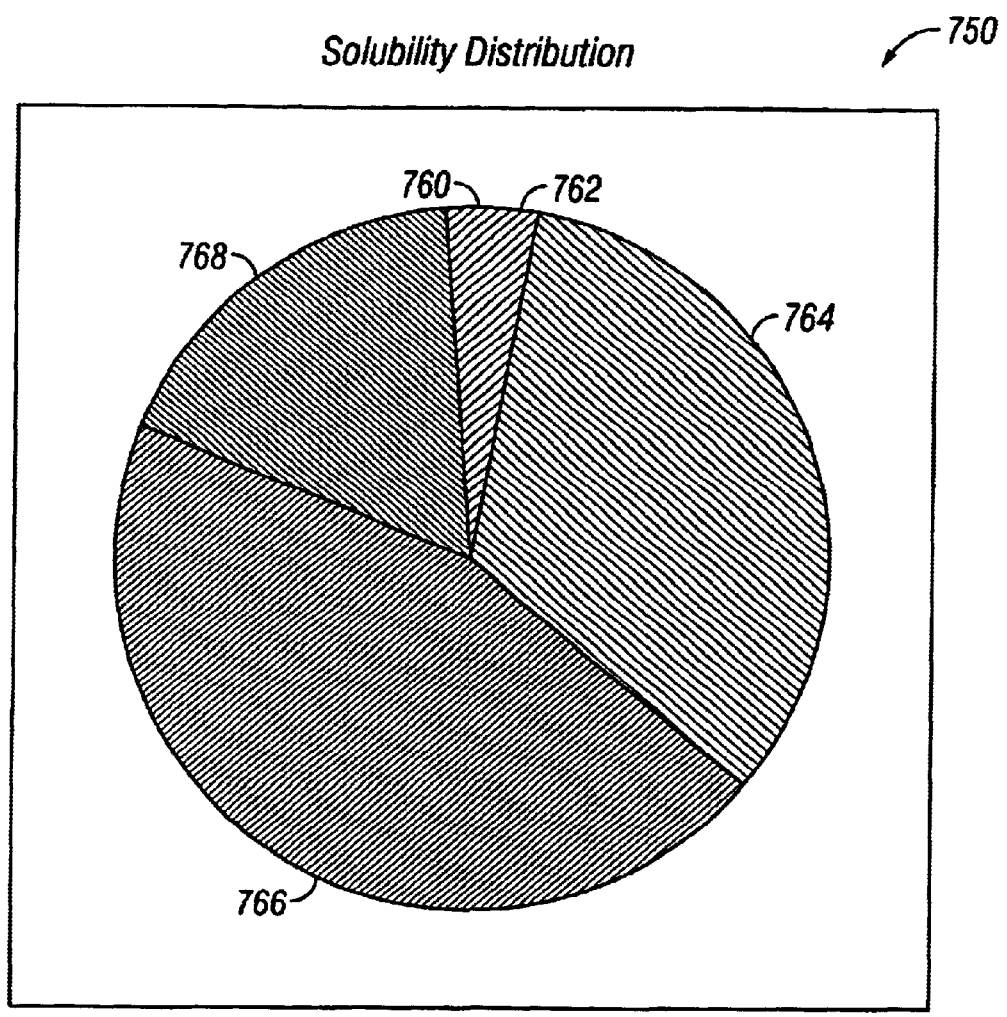
FIG. 7 is a chart illustrating an exemplary solubility distribution profile.

On a larger scale, application of the aforementioned ranking scheme may also be used to construct a solubility profile for a plurality of compounds representing a synthesized library, a virtual library, or substantially any compound collection for which solubilities may be predicted. FIG. 7 illustrates one manner of representing a solubility profile 750 for a diverse collection of compounds for which solubility values have been predicted. In one aspect, the solubility profile 750 for the compound collection provides an easy to interpret summary of the distribution of solubilities for each of the compounds contained within the collection. In the illustrated pie chart, each "slice" 762–768 may represent a selected solubility class or rank of compound solubility which may be further associated with a percentile quantity indicative of how many of the compounds fall within the selected solubility class or rank. In addition, the compounds which make up the library or collection may be subdivided into various sub-libraries and assessed independently of one another to provide still further refined predictive information and solubility characterizations.

It will be appreciated that the various examples of compound solubility classification described above may significantly aid in library design efforts. In one aspect, these methods of solubility classification facilitate the resolution and understanding of the relationship between a compound's structural characteristics and the compound's solubility. This information may further be useful in library design where individual compounds of the library may be selected in such a manner so as to optimize the solubility profile 750.

As previously described, the aforementioned regression models for solubility prediction may be used in conjunction with the solubility equation to rapidly compute the solubility for many molecules in an efficient manner. In various embodiments using the reduced descriptor solubility equation reduces the complexity of the solubility prediction without sacrificing a substantial amount of accuracy. Anticipated calculation rates and throughout for compound solubility analysis may therefore be substantially improved over existing methods of solubility prediction including those which incorporate three dimensional structure information. As a result of the reduced computation time required to predict compound solubility, improvements in performance of data mining operations and predictive library design can be readily achieved.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated may be made by those skilled in the art without departing from the scope of the present invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A method for solubility determination of at least one candidate compound, the method comprising:
   identifying a plurality of descriptors forming an initial descriptor set wherein each descriptor relates to a property of the candidate compound;
   performing a correlation analysis to identify a plurality of substantially correlated descriptors within the initial descriptor set;
   forming a reduced descriptor set from the initial descriptor set wherein selected correlated descriptors are retained from the plurality of substantially correlated descriptors, and wherein at least one retained descriptor comprises a composite descriptor <HBD>*<HBA> wherein <HBD> is a descriptor representing the number of hydrogen bond donors in the candidate compound and <HBA> is a descriptor representing the number of hydrogen bond acceptors in the candidate compound;
   identifying solubility information and descriptor values associated with the reduced descriptor set for a plurality of known compounds forming a training data set;
   identifying a solubility equation based on a selected subset of descriptors contained in the reduced descriptor set and derived using the solubility information and descriptor values for the plurality of known compounds contained in the training data set; and
   applying the solubility equation to the descriptor information for the at least one candidate compound to thereby determine the solubility for the at least one candidate compound.

2. The method of claim 1, further comprising the step of validating the solubility equation by:
   selecting at least one compound forming a validation data set wherein solubility information and descriptor values are known for the at least one compound in the validation data set;
   applying the solubility equation using the known descriptor values for the at least one compound contained in the validation data set;
   comparing the predicted solubility obtained from the solubility equation to the known solubility information; and
   assessing the accuracy of solubility determination based on the results of the comparison of solubilities.

3. The method of claim 2, further comprising the step of performing an iterative refinement of the solubility equation by:
   identifying the selected subset of descriptors forming the previously identified solubility equation as a subsequent initial descriptor set;
   forming a refined solubility equation using the subsequent initial descriptor set;
   assessing the accuracy of solubility determination for the refined solubility equation;
   comparing the accuracy of solubility determination for the refined solubility equation to the accuracy of solubility determination for the previously identified solubility equation; and
   selecting the more accurate solubility equation identified by the comparison as a final solubility equation.

4. The method of claim 1, wherein performing the correlation analysis further comprises the steps of:
   identifying one or more pair-wise correlation coefficients between each of the descriptors contained within the initial descriptor set;
   determining which descriptors contained within the initial descriptor set are correlated; and
   selecting a single descriptor from the correlated descriptors to represent the correlated descriptors.

5. The method of claim 4, wherein a threshold correlation coefficient is identified and used to evaluate the pair-wise correlation coefficients and determine the correlation between descriptors contained within the initial descriptor set.

6. The method of claim 5, wherein the value of the threshold correlation coefficient is between approximately 0.8 and 1.0.

7. The method of claim 1, wherein the descriptors further comprise compound characteristics selected from the group consisting of structural, topological, electronic, and spatial parameters.

8. The method of claim 1, wherein the descriptors further comprise quantitative structure property relationships for each compound.

9. The method of claim 1, wherein the descriptors further comprise two-dimensional descriptors.

10. The method of claim 1, wherein the solubility equation is formed without the use of three dimensional descriptors.

11. The method of claim 1, wherein at least some of the plurality of known compounds that form the training data set contain functional groups selected from the group consisting of alkanes, alkenes, alkynes, halogen derivatives, aromatics, nitros, nitrites, amides, amines, alcohols, ketones, aldehydes, esters, ethers and acids.

12. The method of claim 1, wherein at least some of the plurality of known compounds that form the training data set contain multiple functional groups.

13. The method of claim 1, wherein at least some of the plurality of known compounds that form the training data set contain functional groups that are selected to be similar to those contained in the at least one candidate compound.

14. The method of claim 1, further comprising the step of identifying at least one weak descriptor by:
   identifying descriptors in the initial descriptor set having a reduced solubility correlation for a selected number of compounds in the training data set; and
   removing the at least one weak descriptor from consideration in the reduced descriptor set.

15. The method of claim 1, wherein the solubility equation is identified by performing a statistical analysis of the reduced descriptor set using the training data set to identify a combination of descriptors that possess a selected degree of statistical significance.

16. The method of claim 15, wherein the statistical analysis comprises a modified partial least squares approach that integrates genetic algorithmic evaluation.

17. The method of claim 15, wherein the statistical analysis comprises a stepwise regression analysis approach.

18. The method of claim 1, wherein the solubility equation is characterized by a substantially linear equation.

19. The method of claim 1, wherein the solubility equation comprises approximately 4–12 descriptors.

20. The method of claim 1, further comprising the step of performing a solubility ranking for the at least one candidate compound that classifies the predicted solubility of the at least one candidate compound according to one or more designated solubility ranges.

21. The method of claim 20, wherein solubility ranking is used to classify the predicted solubilities for a plurality of candidate compounds with respect to one another.

22. The method of claim 21, wherein solubility ranking of the plurality of candidate compounds is used to screen for compound subsets that posses desirable solubility characteristics.

23. The method of claim 22, wherein the solubility ranking of the plurality of candidate compounds is used as a screening tool for drug discovery.

24. A method for solubility prediction comprising:
   selecting a first plurality of descriptors comprising identifiable compound properties and characteristics;
   forming a correlated descriptor subset from the first plurality of descriptors wherein the correlated descriptor subset comprises selected descriptors identified by correlation analysis, and wherein at least one selected descriptor comprises a composite descriptor <HBD>*<HBA> wherein <HBD> is a descriptor representing the number of hydrogen bond donors in a compound and <HBA> is a descriptor representing the number of hydrogen bond acceptors in a compound;
   generating a solubility prediction function comprising selected descriptors from the correlated descriptor subset identified by statistical analysis of the correlated descriptor subset using a training data set; and
   applying the solubility prediction function to predict a compound's solubility on the basis of descriptor information for the compound.

25. The method of claim 24, wherein the first plurality of descriptors comprise compound characteristics selected from the group consisting of structural, topological, electronic, and spatial parameters.

26. The method of claim 24, wherein the first plurality of descriptors comprise compound quantitative structure property relationships.

27. The method of claim 24, wherein the first plurality of descriptors comprise two-dimensional descriptors.

28. The method of claim 24, wherein the first plurality of descriptors exclude three-dimensional descriptors.

29. The method of claim 24, wherein the first plurality of descriptors describe the chemical and physical characteristics for a plurality of compound types.

30. The method of claim 24, wherein the training data set comprises a plurality of compounds having known solubilities and descriptors.

31. The method of claim 30, wherein the plurality of compounds that form the training data set possess characteristics similar to compounds whose solubility is to be predicted using the solubility prediction function.

32. The method of claim 31, where the characteristics for the compounds that form the training data set include functional group characteristics.

33. The method of claim 32, wherein the functional characteristics are selected from the group consisting of alkanes, alkenes, alkynes, halogen derivatives, aromatics, nitros, nitriles, amides, amines, alcohols, ketones, aldehydes, esters, ethers and acids.

34. The method of claim 32, wherein the functional group characteristics comprise characteristics from multiple functional groups.

35. The method of claim 24, wherein correlation analysis comprises assessing the correlation between at least two of the first plurality of descriptors and wherein the selected descriptor is retained from the descriptors that are correlated.

36. The method of claim 35, wherein the correlated descriptor subset comprises a plurality of selected descriptors retained from a plurality of correlation assessments.

37. The method of claim 24, wherein the correlated descriptor subset further comprises other descriptors in addition to the selected descriptors.

38. The method of claim 24, wherein the correlation analysis further comprises the steps of:
   identifying pair-wise correlation coefficients between the first plurality of descriptors;
   identifying a threshold correlation coefficient;
   identifying correlated descriptors in the first plurality of descriptors as descriptors having pair-wise correlation coefficients that exceed the threshold correlation coefficient; and
   identifying the selected descriptor from the correlated descriptors.

39. The method of claim 38, wherein the value of the threshold correlation coefficient is between approximately 0.8 and 1.0.

40. The method of claim 24, wherein the statistical analysis used to generate a solubility prediction function comprises a regression analysis of the training data set to identify a combination of selected descriptors from the correlated descriptor subset that describe the solubility for compounds contained within the training data set with a desired degree of accuracy.

41. The method of claim 40, wherein the statistical analysis comprises a stepwise regression analysis in which the solubility prediction function is generated by incrementally increasing the number of selected descriptors used to generate the solubility prediction function until the desired degree of accuracy is achieved.

42. The method of claim 41, wherein the accuracy of the solubility prediction equation is evaluated by comparing actual versus predicted solubilities for the training set data.

43. The method of claim 24, further comprising the step of performing a solubility ranking wherein a compound's predicted solubility is classified according to one or more designated solubility ranges.

44. The method of claim 43, wherein solubility ranking is used to classify the predicted solubilities for a plurality of compounds with respect to one another.

45. The method of claim 44, wherein solubility ranking is used to screen for compound subsets that possess desirable solubility characteristics.

46. The method of claim 45, wherein solubility ranking is used as a screening tool for drug discovery.

47. The method of claim 24, wherein the solubility prediction function is used to screen virtual libraries of compounds or molecules for desirable solubility characteristics.

48. The method of claim 24, wherein the solubility prediction function is used as a data mining tool for evaluating the solubilities for compound or molecular libraries.

49. A method for descriptor construction to be used in solubility analysis applications, the method comprising:
   selecting a compound or molecular structure;
   determining the number of hydrogen bond donors <HBD> in the selected compound or molecular structure;
   determining the number of hydrogen bond acceptors <HBA> in the selected compound or molecular structure;
   determining the product of the number of hydrogen bond donors and the number of hydrogen bond acceptors <HBD>*<HBA>; and
   associating the product of the number of hydrogen bond donors and the number of hydrogen bond acceptors <HBD>*<HBA> with a first solubility descriptor for the selected compound or molecular structure.

50. The method of claim 49, wherein the first solubility descriptor is incorporated into a solubility prediction equation.

51. The method of claim 50, wherein the solubility prediction equation further comprises other solubility descriptors.

52. The method of claim 50, wherein values for the solubility descriptors are determined by evaluating training set information comprising selected compounds with known solubilities and descriptor values.

53. The method of claim 50, wherein the solubility prediction equation is used to predict the solubility of one or more additional compounds or molecules for which the solubility descriptor and the plurality of other descriptors are identifiable.

54. The method of claim 50, wherein at least one of the other solubility descriptors comprises a hydrogen bond donor assessment.

55. The method of claim 50, wherein at least one of the other solubility descriptors comprises a water-octanol partition coefficient.

56. The method of claim 50, wherein each descriptor is further associated with a scaling factor that provides a weighted contribution to the solubility prediction equation.

57. The method of claim 56, wherein each scaling factor comprises a value between approximately −1.0 and +1.0.

58. The method of claim 56, wherein the scaling factors are determined by evaluating training set information comprising selected compounds with known solubilities and descriptor values.

59. The method of claim 56, wherein the solubility prediction equation is defined according to the relationship; $Coeff_1*<AlogP98>+Coeff_2*<HBD>*<HBA>+Coeff_3*<Zagreb>+Coeff_4*<S\_aaaC>+Coeff_5*<Rotlbonds>+Coeff_6*<HBD>+Coeff_7*<S\_sOH>+Coeff_8*<Wiener>$ wherein '$Coeff_x$' is representative of a selected scaling factor and wherein <AlogP98> comprises a water-octanol partition coefficient descriptor, <Zagreb> comprises a topological descriptor represented by a sum of the squares of vertex valencies, <S_aaaC> comprises an electrotopological descriptor represented by carbon atoms with three aromatics bonds, <Rotlbonds> comprises a descriptor for rotatable bond number, <S_sOH> comprises an electrotopological descriptor represented by singly bonded hydroxyl groups, and <Wiener> comprises a topological descriptor represented by the sum of chemical bonds between heavy atoms.

60. The method of claim 50, wherein the descriptors comprise compound characteristics selected from the group consisting of structural, topological, electronic, and spatial parameters.

61. The method of claim 50, wherein the descriptors comprise compound quantitative structure property relationships.

62. The method of claim 50, wherein the descriptors comprise two-dimensional descriptors.

63. The method of claim 50, wherein the descriptors exclude three-dimensional descriptors.

64. The method of claim 50, wherein the descriptors describe the chemical and physical characteristics for a plurality of compound types.

65. A system for assessing the solubility of at least one compound, the system comprising:

a descriptor identification component that identifies a plurality of descriptors describing properties and characteristics for the at least one compound;

a correlation analysis component that evaluates correlations between the plurality of descriptors to identify correlated descriptor groups and further identifies at least one selected descriptor to represent one or more of the correlated descriptor groups, wherein at least one identified descriptor comprises a composite descriptor <HBD>*<HBA> wherein <HBD> is a descriptor representing the number of hydrogen bond donors in a compound and <HBA> is a descriptor representing the number of hydrogen bond acceptors in a compound; and a solubility modeling component that uses the at least one selected descriptor to form a solubility prediction equation using a training data set for which solubility and selected descriptor information is known.

66. The system of claim 65, wherein the descriptor identification component identifies descriptors comprising compound characteristics selected from the group consisting of structural, topological, electronic, and spatial parameters.

67. The method of claim 65, wherein the descriptor identification component identifies descriptors comprising compound quantitative structure property relationships.

68. A method of predicting the solubility of a compound in a solvent, the method comprising:

counting the number of hydrogen bond donors in each molecule of said compound;

counting the number of hydrogen bond acceptors in each molecule of said compound;

multiplying said counts to produce a descriptor value;

multiplying said descriptor value by a scaling factor to produce a first term of an equation; and adding said term to other terms of said equation to produce a predicted solubility value.

69. The method of claim 68, additionally comprising multiplying the count of hydrogen bond donors by a constant to produce a second term of said equation.

70. The method of claim 68, wherein said equation is represented by a substantially linear relationship described by the summation of terms.

71. A computer readable medium having stored thereon instructions which cause a general purpose computer to perform a method of generating a predicted solubility value for a selected compound, said method comprising:

counting the number of hydrogen bond donors in each molecule of said compound;

counting the number of hydrogen bond acceptors in each molecule of said compound;

multiplying said counts to produce a descriptor value;

multiplying said descriptor value by a constant to produce a first term of an equation; and adding said term to other terms of said equation.

72. The method of claim 71, wherein said equation is represented by a substantially linear relationship described by the summation of terms.

* * * * *